United States Patent [19]
Takeuchi et al.

[11] Patent Number: 5,498,735
[45] Date of Patent: Mar. 12, 1996

[54] PROCESS OF PRODUCING ALPHA-OLEFIN

[75] Inventors: Kunio Takeuchi, Shinnanyo; Takao Tamura, Sodegaura; Hironori Tashiro, Tokuyama, all of Japan

[73] Assignee: Idemitsu Petrochemical Co., Ltd., Tokyo, Japan

[21] Appl. No.: 276,267

[22] Filed: Jul. 18, 1994

[30] Foreign Application Priority Data

Aug. 5, 1993 [JP] Japan .................................. 5-212163
Sep. 22, 1993 [JP] Japan .................................. 5-257535

[51] Int. Cl.$^6$ .............................. C07F 5/06; C07C 2/02
[52] U.S. Cl. .......................... 556/187; 556/190; 585/328; 585/522
[58] Field of Search ............................ 556/190, 187; 585/328, 522

[56] References Cited

U.S. PATENT DOCUMENTS

| | | | |
|---|---|---|---|
| 2,889,385 | 6/1959 | Catterall et al. | 260/683.15 |
| 3,278,633 | 10/1966 | Serratore et al. | 260/683.15 |
| 3,358,050 | 12/1967 | Acciarri et al. | 260/683.15 |
| 3,389,161 | 6/1968 | Koltong et al. | 260/448 |
| 3,412,126 | 11/1968 | Gautreaux | 260/448 |
| 3,499,057 | 3/1970 | Serratore | 260/683.15 |
| 3,663,647 | 5/1972 | Lanier | 260/683.15 D |
| 4,935,569 | 6/1990 | Harkins et al. | 585/328 |
| 5,049,687 | 9/1991 | Abazajian | 556/190 |
| 5,210,338 | 5/1993 | Samsel | 568/911 |

FOREIGN PATENT DOCUMENTS 3-48630   3/1991   Japan .

*Primary Examiner*—Porfirio Nazario-Gonzales
*Attorney, Agent, or Firm*—Frishauf, Holtz, Goodman, Langer & Chick

[57] ABSTRACT

A process of producing an α-olefin which comprises carrying out separately the growth of ethylene with triethyl aluminum and the growth of ethylene with tributyl aluminum, displacing the resulting higher trialkyl aluminum with ethylene, thereby forming triethyl aluminum and an α-olefin, and displacing at least part of the resulting triethyl aluminum with butene contained in the resulting α-olefin, thereby forming tributyl aluminum.

The present invention permits the efficient production of α-olefins containing linear α-olefins in extremely high purity. The α-olefins will find use as comonomers for polyolefins (whose demand is increasing recently) and also as raw materials of synthetic lubricants.

13 Claims, 1 Drawing Sheet

/* 5,498,735 */

PROCESS OF PRODUCING ALPHA-OLEFIN

BACKGROUND OF THE INVENTION

The present invention relates to a process of producing an α-olefin and, more particularly, to a process of producing an α-olefin containing a linear α-olefin in high purity.

An α-olefin is an olefin oligomer of carbon number 4 to 18 which has a straight-chain (unbranched) molecular structure in which there is a double bond at the α position. An α-olefin, especially the one containing a linear α-olefin in high purity, finds use as a monomer to modify polyolefins or as a raw material for synthetic lubricants, plasticizers, and surface active agents. Especially, those of carbon number 6 to 10 are in general use. For example, an α-olefin of carbon number 6 to 8 is used mainly as a comonomer of polyolefins. It is required to be linear and highly pure, and it enjoys a large demand. Also, there is in an increasing demand for an α-olefin of carbon number 10 or so as a raw material for synthetic lubricants.

An α-olefin is produced conventionally by polymerization of ethylene by the use of a Ziegler catalyst. There are two known processes: one gives rise to an α-olefin whose molecular weight distribution obeys the Schultz-Flory distribution, and the other gives rise to an α-olefin whose molecular weight distribution obeys the Poisson distribution. The former process usually employs a titanium-based catalyst or a zirconium-based catalyst to convert ethylene into an α-olefin oligomer. Its advantage is the ability to give rise to an α-olefin containing a linear α-olefin in high purity (with small amounts of branched α-olefin). On the other hand, it suffers the disadvantage of giving rise to an α-olefin whose molecular weight distribution is usually broad and obeys the Schultz-Flory distribution. If it is used to produce an α-olefin of carbon number 10 or below in large amounts which has a comparatively narrow molecular weight distribution, the resulting product contains α-olefins of carbon number 4 to 6 (such as butene) in an extremely large amount. In other words, it is not suitable for the efficient production of α-olefins of carbon number 10 or below, which find use as a comonomer of polyolefins or a raw material of synthetic lubricants.

On the other hand, there is a process of oligomerizing ethylene into an α-olefin by the use of trialkyl aluminum (such as triethyl aluminum and tributyl aluminum). It offers the advantage of giving rise to an α-olefin whose molecular weight distribution obeys the Poisson distribution and selectively giving rise to an α-olefin of carbon number 10 or below. In addition, there has been proposed a process of recycling the resulting butene, thereby reducing the amount of butene produced. (See Japanese Patent Laid-open No. 48630/1991.)

This process consists of performing the growth of ethylene with trialkyl aluminum at a comparatively low temperature under high pressure, thereby forming a higher trialkyl aluminum, replacing a large part of the higher trialkyl aluminum with ethylene at a comparatively high temperature under low pressure, thereby forming an α-olefin and regenerating triethyl aluminum, replacing the remaining higher trialkyl aluminum with butene contained in the thus formed α-olefin, thereby forming an α-olefin and tributyl aluminum, and performing the growth of ethylene with tributyl aluminum. Thus, butene is consumed for the formation of tributyl aluminum, and the final product is an α-olefin of carbon number 6 or above. The disadvantage of recycling butene is that the resulting α-olefin contains branched α-olefins, with the purity of linear α-olefins being low.

The present inventors found that the low purity of α-olefins produced by the above-mentioned process arises from the displacement of higher trialkyl aluminum with butene (which is carried out to recycle butene) and the separation by distillation of the product formed by displacement. They investigated the steps of utilizing the butene in a different manner than mentioned above, and the result of the investigation led to the present invention.

SUMMARY OF THE INVENTION

It is an object of the present invention to provide a process of producing an α-olefin which comprises carrying out separately the growth (growth reaction) of ethylene with triethyl aluminum and the growth of ethylene with tributyl aluminum, replacing the resulting higher trialkyl aluminum with ethylene, thereby forming triethyl aluminum and an α-olefin, and displacing at least part of the resulting triethyl aluminum with butene contained in the resulting α-olefin, thereby forming tributyl aluminum.

DESCRIPTION OF THE PREFERRED EMBODIMENTS

[Growth of Ethylene]

Figure 1:
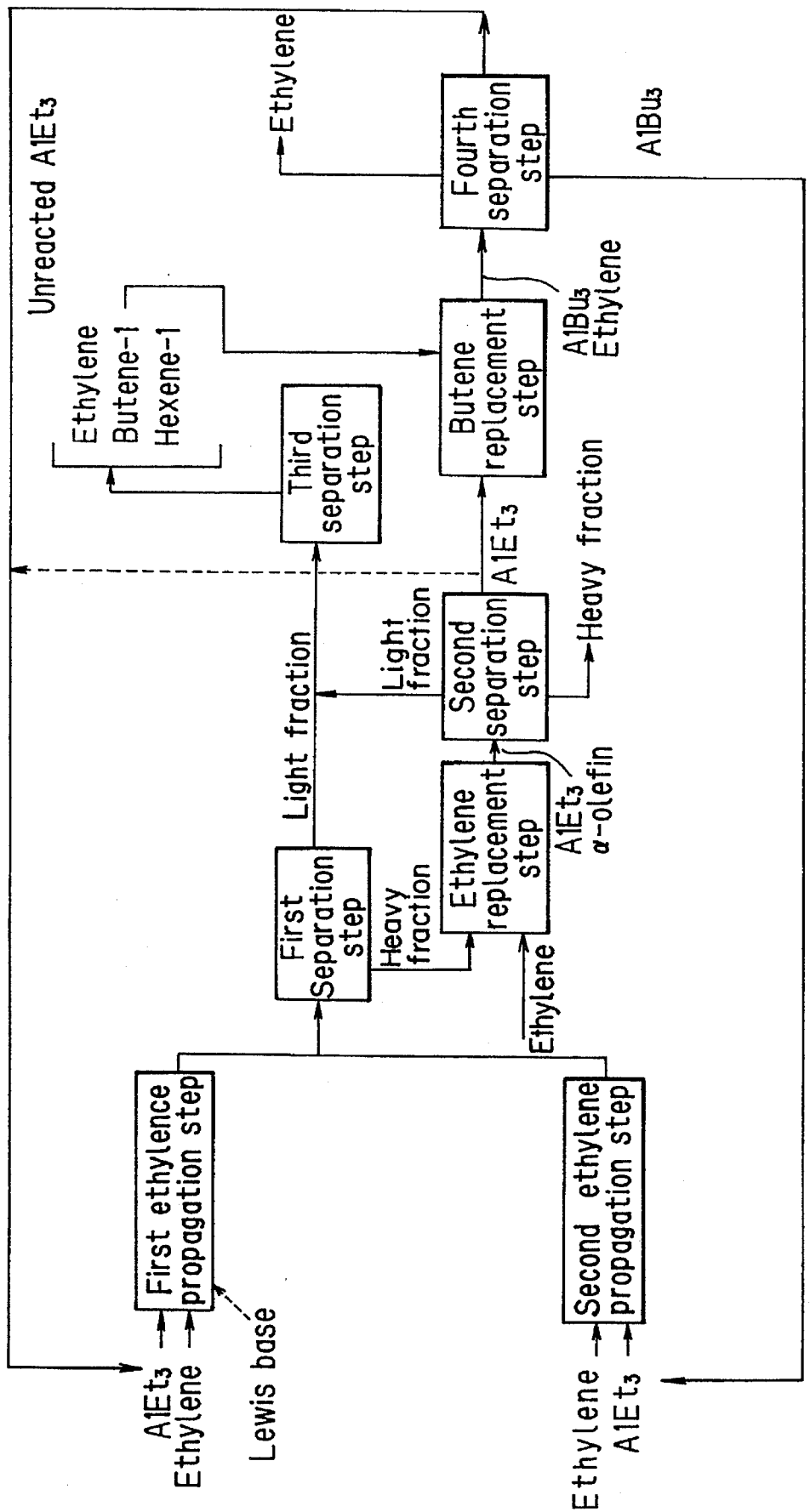
FIG. 1 is a flow diagram showing an embodiment of the present invention. The flow consists of supplying all of triethyl aluminum to the butene replacement step, recycling unreacted triethyl aluminum to the first ethylene growth step, and recycling tributyl aluminum to the second ethylene growth step. The broken line in the diagram means that the triethyl aluminum obtained in the third separation step may be recycled to the first ethylene growth step. According to this embodiment, the light fraction from the second separation step is mixed with the light fraction from the first separation step and the resulting mixture is separated into ethylene and α-olefins of carbon number 4 and above by distillation in the third separation step.

According to the present invention, it is necessary to carry out separately the growth of ethylene with triethyl aluminum and the growth of ethylene with tributyl aluminum.

The growth of ethylene with triethyl aluminum is accomplished by the first ethylene growth step which involves the reaction of ethylene with triethyl aluminum in the first ethylene growth reactor to give higher trialkyl aluminum and an α-olefin.

That is, the first ethylene growth reactor is charged with ethylene and triethyl aluminum (abbreviated as TEA hereinafter) so that higher trialkyl aluminum and an α-olefin are formed. The growth of ethylene should be accomplished in a molar ratio of TEA to ethylene in the range from ½ to ¹⁄₁₀₀, at a reaction temperature of 80°–150° C., preferably 90°–120° C., and at a reaction pressure of 100–350 kg/cm²G. preferably 150–250 kg/cm²G. The residence time should be long enough for the alkyl chain bonded to the aluminum atom to grow up to carbon number 6–12. It is usually 15 minutes to 6 hours, depending on the reaction temperature and pressure. The reactor may be of tubular type or vessel type, the former being preferable.

Incidentally, the first ethylene growth step should preferably be carried out in the presence of a Lewis base. Examples of the Lewis base include disulfides [$(RS)_2$], sulfides [$(R_2S)$], ethers [$(R_2O)$], tertiary phosphines [$(R_3P)$], phosphine oxides [$(R_3PO)$], and tertiary amines [$(R_3N)$].

As Lewis base, it is preferable to use at least one compound selected from the group consisting of disulfides, sulfides, ethers, tertiary phosphines and tertiary amines. Definite examples of such Lewis base are shown below.

Disulfides include $C_2H_5SSC_2H_5$, $C_{12}H_{25}SSC_{12}H_{25}$, and PhSSPh. Sulfides include $C_2H_5SC_2H_5$, $C_4H_9SC_4H_9$, and PhSPh. Ethers include $C_2H_5OC_2H_5$, $C_3H_7OC_3H_7$, and PhOPh. Tertiary phosphines include $(C_2H_5)_3P$, $(C_4H_9)_3P$, and $(C_6H_5)_3P$. Phosphine oxides include $(C_2H_5)_3P=O$ and $Ph_3PO$. Tertiary amines include $(C_2H_5)_3N$ and $(C_6H_{13})_3N$. (Ph denotes a phenyl group.) They may be used alone or in combination with one another. The Lewis base should be used in an amount of 5 1000 mol % of TEA.

The reaction may be carried out in the presence or absence of solvent. Preferred solvents include aliphatic hydrocarbons (such as n-hexane and cyclohexane) and aromatic hydrocarbons (such as benzene and toluene). The reaction may be carried out batchwise, continuously, or semicontinuously.

The Lewis base accelerates the reaction of ethylene with TEA with stirring under the above-mentioned conditions, forming higher trialkyl aluminum efficiently at a high rate of growth at a comparatively low temperature. That is, according to such method, a rate of growth of TEA is high at a comparatively low temperature. This means that the reaction can be carried out economically using a reactor of small capacity.

The reaction in the presence of a Lewis base permits the production of higher trialkyl aluminum at a comparatively low temperature. This leads to the advantage that the reaction gives rise to an α-olefin in a small amount and the α-olefin that is formed after replacement is of high purity.

The growth of ethylene with tributyl aluminum is accomplished by the second ethylene growth step which involves the reaction of ethylene with tributyl aluminum in the second ethylene growth reactor to give higher trialkyl aluminum and an α-olefin. That is, the second ethylene growth reactor is charged with ethylene and tributyl aluminum so that higher trialkyl aluminum and an α-olefin are formed.

In the second ethylene growth step, tributyl aluminum (abbreviated as TBA hereinafter) and ethylene are introduced into the second ethylene growth reactor to give higher trialkyl aluminum and an α-olefin. The conditions for growth is almost identical to those for the first ethylene growth step.

[Displacement with Ethylene]

According to the present invention, the growth of ethylene with triethyl aluminum is carried out separately from the growth of ethylene with tributyl aluminum, and the resulting trialkyl aluminum undergoes replacement with ethylene.

To be more specific, the present invention involves the first and second ethylene growth steps, which are followed by the first separation step and the ethylene displacement step. The first ethylene growth step involves the reaction of ethylene with triethyl aluminum in the first ethylene growth reactor which gives rise to an α-olefin and higher trialkyl aluminum. The second ethylene growth step involves the reaction of ethylene with tributyl aluminum in the second ethylene growth reactor which gives rise to an α-olefin and higher trialkyl aluminum. In the first separation step, the reaction products from the first and second ethylene growth steps are separated by distillation, individually or all together, into a light fraction containing no higher trialkyl aluminum and a heavy fraction containing higher trialkyl aluminum. The thus obtained higher trialkyl aluminum undergoes displacement with ethylene.

In the first separation step, the products containing the higher trialkyl aluminum formed by the first and second ethylene growth steps are mixed and distilled or distilled separately without mixing, so that they are separated into a light fraction containing unreacted ethylene and α-olefins of carbon number up to 10 or 12 and a heavy fraction containing higher trialkyl aluminum and α-olefins of carbon number 12 or 14 or above. Whether the light fraction contains α-olefins of carbon number up to 10 or 12 depends on the conditions of distillation, especially pressure. For appropriate operation, the pressure in the distillation column should be 10–400 Torr and the temperature at the bottom of the column should be 120°–200° C.

The higher trialkyl aluminum, which is obtained in the first separation step, subsequently undergoes displacement with ethylene.

This reaction is carried out in the ethylene displacement step which is designed to react, in the ethylene displacement reactor, ethylene with the heavy fraction separated in the first separation step, to give triethyl aluminum and an α-olefin.

That is, in the ethylene displacement step, ethylene and a heavy fraction separated in the first separation step are introduced in the ethylene displacement reactor to give triethyl aluminum and an α-olefin.

The ethylene displacement reaction should be carried out under the condition that the molar ratio of higher trialkyl aluminum to ethylene is from ½ to ¹⁄₁₀₀, the temperature is 180°–350° C. (preferably 270°–320° C.), the pressure is 1–100 kg/cm²G (preferably 2–30 kg/cm²G), and the residence time is 0.1–5 seconds (because the displacement reaction proceeds in an extremely short time). The reactor is usually of tubular type. It is necessary that complete mixing be ensured in the reactor. [Displacement with Butene]

The ethylene displacement reaction mentioned above gives rise to triethyl aluminum and α-olefins. The thus formed triethyl aluminum undergoes at least partly displacement with butene contained in the resulting α-olefins, so that tributyl aluminum is formed. The butene displacement reaction follows the ethylene displacement reaction. Before the butene displacement reaction, the two separation steps (i.e., the second and third separation steps) undergoes.

The second separation step is designed to separate by distillation the product obtained in the ethylene displacement step into TEA, a TEA-free light fraction, and a TEA-free heavy fraction. The light fraction usually contains unreacted ethylene and α-olefins of carbon number up to 10 or 12. The heavy fraction usually contains an α-olefin of carbon number 12, 14, or 16. Whether the light fraction contains α-olefins of carbon number up to 10 or 12 depends on the conditions of distillation, especially pressure.

The separated TEA is entirely or partly introduced into the butene displacement step (mentioned later). It may also be partly recycled to the first ethylene growth step. Incidentally, distillation in the second separation step may be carried out under the same conditions as in the first separation step.

The light fractions from the first and second separation steps are distilled after mixing or distilled separately without mixing, in the third separation step, so that they are separated into α-olefins such as unreacted ethylene, butene-1, hexene-1, octene-1, and decene-1. It is desirable to perform mixing prior to distillation because the light fraction from the second separation step exceeds that from the first separation step.

The separated butene-1 is usually used for replacement with butene (mentioned below). However, if necessary, it may be recovered as a product. The separated ethylene may be reused as a feedstock for ethylene growth or ethylene displacement reaction. The separated α-olefins of carbon number 6 to 10 (or 6 to 12) are recovered as final products to be used as a comonomer for polyolefins.

After the second separation step and the third separation step, into the butene displacement reactor are introduced at least part of the triethyl aluminum obtained in the second separation step and the butene-1 obtained in the third separation step, so that tributyl aluminum and ethylene are formed by butene displacement.

The butene displacement reaction may be carried out under almost the same conditions as those for the above-mentioned ethylene displacement reaction. in the butene displacement reaction, TEA is reacted with butene-1 (in the butene-1 fraction) in the substantial absence of other olefins to give a reaction product composed of tributyl aluminum, ethylene, and unreacted butene-1. The reaction product hardly contains branched α-olefins. In other words, the resulting linear α-olefins are of high purity.

In the fourth separation step, the reaction product obtained in the butene displacement step is distilled for separation of tributyl aluminum and ethylene (and unreacted butene-1, if necessary).

The separation of tributyl aluminum (which has a comparatively high boiling point) from ethylene and butene-1 (which have a comparatively low boiling point) can be accomplished readily at a relatively low temperature. The separation by distillation hardly forms any substance which lowers the purity of the linear α-olefins. Distillation should be carried out at 760 Torr and 20°–100° C. (at the bottom of the column) so as to give tributyl aluminum of high purity.

The thus obtained tributyl aluminum is usually recycled to the second ethylene growth step. On the other hand, the unreacted triethyl aluminum is usually recycled to the first ethylene growth step. In this way, the triethyl aluminum and tributyl aluminum obtained in the ethylene displacement reaction and/or the butene displacement reaction are usually recycled to the ethylene growth steps.

The process of the present invention may be supplemented with the following steps, if necessary.

[Hexene Displacement Step]

In this step, into hexane displacement reactor are introduced the hexene-1 obtained in the third separation step and part of the TEA obtained in the second separation step so as to yield trihexyl aluminum and ethylene. Usually the reaction product also contains unreacted hexene-1. This step is intended to make the final product to contain no or a little hexene-1 by recycling hexene-1 fraction obtained in the third separation step. The hexene displacement may be accomplished under almost the same conditions as for the above-mentioned ethylene displacement step.

[Fifth Separation Step]

This step is intended to separate the product obtained in the hexene displacement step into trihexyl aluminum and ethylene by distillation. This step is also intended to distill away unreacted hexene-1, if it is present. Their separation is easy to carry out because trihexyl aluminum has a higher boiling point than ethylene and hexene, and the separated trihexyl aluminum has a high purity. Distillation should be carried out at 760 Torr and 60°–120° C. (at the bottom of the column). The thus separated trihexyl aluminum may be recycled to the third ethylene growth step.

[Third Ethylene Growth Step]

In this step, into third ethylene growth reactor are introduced the trihexyl aluminum and ethylene obtained in the fifth separation step so as to form higher trialkyl aluminum and α-olefins by ethylene growth reaction. The ethylene growth step may be carried out under almost the same conditions as those for the above-mentioned first ethylene growth step.

EXAMPLES

The invention will be described in more detail with reference to the following examples.

Example 1

(1) Ethylene growth was carried out by supplying a tubular reactor with TEA and ethylene in a molar ratio of 1:50 (TEA/ethylene) at 100° C. and 200 kg/cm$^2$G such that the average residence time was 4 hours. There was obtained higher trialkyl aluminum whose carbon distribution obeys the Poisson distribution, with the average carbon number being 6–8.

(2) Ethylene growth was carried out by supplying a tubular reactor (of the same type as used in (1) above) with tri-n-butyl aluminum and ethylene in a molar ratio of 1:50 (TBA/ethylene) at 100° C. and 200 kg/cm$^2$G such that the average residence time was 3 hours. There was obtained higher trialkyl aluminum whose carbon distribution obeys the Poisson distribution, with the average carbon number being 6–8.

(3) The products obtained in (1) and (2) above were mixed, and the mixture was distilled at 130° C. and 200 mmHg for separation into α-olefins (composed of ethylene fraction to decene-1 fraction) and higher trialkyl aluminum (containing higher boiling fractions than dodecene).

(4) The bottom product obtained by separation in (3) above was provided with ethylene in a molar ratio of 1:10 (the bottom product/ethylene), and ethylene displacement was carried out at 270° C. and 10 kg/cm$^2$G, with the average residence time being 0.5 second. The conversion of trialkyl aluminum was about 95%. There were obtained α-olefins and triethyl aluminum.

(5) The product obtained in (4) above was distilled at 130° C. and 200 mmHg for separation into α-olefins (composed of ethylene fraction to decene-1 fraction) and triethyl aluminum. The residues of distillation underwent further distillation at 180° C. and 400 mmHg for separation into triethyl aluminum and α-olefins composed of higher boiling fractions than dodecene. About 60% of the triethyl aluminum was recycled to the ethylene growth reactor (1) mentioned above.

(6) The triethyl aluminum obtained in (5) above and the butene-1 obtained in the separation step were introduced in a molar ratio of 10:1 (butene-1/TEA) into the butene displacement reactor. Butene displacement was carried out at 300° C. and 10 kg/cm$^2$G, with the average residence time being 0.5 second. The conversion of higher trialkyl aluminum was about 95%. There were obtained ethylene and tri-n-butyl aluminum.

(7) The ethylene, butene-1, and tri-n-butyl aluminum obtained in (6) above were separated from one another by flash vaporization. The resulting tri-n-butyl aluminum was recycled to the ethylene growth reactor (2) mentioned above.

Thus, there was obtained linear α-olefins (97% purity) composed of the following fractions. (The purity is expressed in terms of the ratio of n-octene in olefins of carbon number 8.)

| | |
|---|---|
| Fraction of carbon number 6 | 40–60 wt % |
| Fraction of carbon number 8 | 20–40 wt % |
| Fraction of carbon number 10 | 5–20 wt % |
| Fraction of carbon number 12 and above | 0–10 wt % |

Comparative Example 1

The same procedure as in Example 1 was repeated to produce α-olefins, except that the higher trialkyl aluminum obtained in the ethylene growth step underwent displacement with butene-1 in the presence of high boiling olefins composed of those fractions of carbon number 12 and above and the product resulting from the displacement reaction underwent separation at 140° C. and 100 mmHg.

The conversion of higher trialkyl aluminum was about 60%. There was obtained linear α-olefins (95% purity) composed of the following fractions.

| | |
|---|---|
| Fraction of carbon number 6 | 30–50 wt % |
| Fraction of carbon number 8 | 20–30 wt % |
| Fraction of carbon number 10 | 10–20 wt % |
| Fraction of carbon number 12 and above | 0–10 wt % |

Example 2

The same procedure as in Example 1 was repeated, except that the triethyl aluminum obtained in (5) of Example 1 and the butene-1 obtained in the separation step were introduced in a molar ratio of 10:1 (butene-1/TEA) into the butene displacement reactor (with the feed rate of butene-1 being 30 ml/hr) and butene displacement was carried out at 300° C. and 2 kg/cm$^2$G, with the average residence time being 1.4 seconds.

The conversion of higher trialkyl aluminum was about 28%. There was obtained a reaction product composed of ethylene and tributyl aluminum (excluding unreacted products). The reaction product does not contain olefins of carbon number 4 and above.

Comparative Example 2

The same procedure as in Example 1 was repeated, except that the trioctyl aluminum (abbreviated as TOA hereinafter) and the butene-1 obtained in the separation step were introduced in a molar ratio of 10:1 (butene-1/TOA) into the butene displacement reactor (with the feed rate of butene-1 being 30 ml/hr) and butene displacement was carried out at 220° C. and 6 kg/cm$^2$G, with the average residence time being 0.3 seconds.

The conversion of higher trialkyl aluminum was about 60%. There was obtained a reaction product composed of octene and tributyl aluminum (excluding unreacted products). The content of 1-octene in the octene was 95.9%.

Butene displacement was carried out under different conditions in Comparative Example 2 and Example 2 because the condition for the former was established so that the octene has a high purity as desired.

In the case that butene displacement in Comparative Example 2 is carried out under the same conditions in Example 2, the purity of resulting octene undergo.

It is noted that Example 2 is superior to Comparative Example 2 in that the butene replacement reaction in the former gives rise to no branched olefins (which leads to the high purity of the resulting α-olefins).

Referential Example 1

A 300-ml autoclave was charged with 11.38 g of Al(Bu)$_3$, 2.32 g of (C$_{12}$H$_{25}$S)$_2$, and 103.0 g of n-tetradecane. The autoclave was charged further with ethylene until the pressure increased to 200 kg/cm$^2$G. Reaction was carried out with stirring at 110° C. for 3 hours. During reaction, the ethylene pressure was kept constant and the molar ratio of ethylene to trialkyl aluminum [Al(Bu)$_3$] was kept at about 10:1 (ethylene/trialkyl aluminum).

After the completion of reaction, the autoclave was cooled to room temperature and the resulting higher trialkyl aluminum was hydrolyzed to give paraffin and part of olefins. The results are shown in Table 1.

Hydrolysis was carried out by stirring the reaction mixture for 5 minutes in five times as much isopropyl alcohol as the molar amount of the higher trialkyl aluminum. The hydrolyzate was acidified with dilute hydrochloric acid until the water phase had pH 2 after stirring for 5 minutes, so that aluminum compounds were transferred to the water phase for removal.

Incidentally, the average molecular weight denotes that of the product (composed of paraffins and olefins) obtained after hydrolysis.

Referential Examples 2 to 11

The same procedure as in Referential Example 1 was repeated except that the conditions were changed as shown in Table 1. The results are shown in Table 1.

Comparative Referential Example 1

The same procedure as in Referential Example 1 was repeated except that the Lewis base was not added. The results are shown in Table 1.

Comparative Referential Example 2

The same procedure as in Referential Example 1 was repeated except that the Lewis base was not added and the conditions shown in Table 1 were used. The results are shown in Table 1.

TABLE 1

| Referential Example No. | Lewis base Kind | Amount* (mol %) | Reaction temperature (°C.) | Reaction time (hours) | Average molecular weight |
|---|---|---|---|---|---|
| 1 | (C$_{12}$H$_{25}$S)$_2$ | 10 | 110 | 3 | 93 |
| 2 | (PhS)$_2$ | 10 | 110 | 3 | 85 |
| 3 | Ph$_2$O | 10 | 110 | 3 | 89 |
| 4 | Ph$_2$O | 100 | 110 | 3 | 94 |
| 5 | Ph$_2$S | 50 | 110 | 3 | 98 |
| 6 | Ph$_2$S | 500 | 110 | 3 | 126 |

TABLE 1-continued

| Referential Example No. | Lewis base Kind | Amount* (mol %) | Reaction temperature (°C.) | Reaction time (hours) | Average molecular weight |
|---|---|---|---|---|---|
| 7 | Ph$_2$S | 500 | 100 | 4 | 130 |
| 8 | Ph$_2$s | 500 | 90 | 4 | 92 |
| 9 | Et$_2$s | 50 | 110 | 3 | 126 |
| 10 | Hx$_3$N | 10 | 110 | 3 | 106 |
| 11 | Bu$_3$P | 10 | 110 | 3 | 98 |
| 1** | none | — | 110 | 3 | 84 |
| 2** | none | — | 90 | 8 | 90 |

*mol % based on the amount of Al(Bu)$_3$
**Comparative Referential Examples

It is noted from Table 1 that the average molecular weight in Referential Examples 1 to 11 is higher than that in Comparative Referential Example 1 in which no Lewis base was used. It is also noted from Table 1 that the average molecular weight in Referential Examples 1 to 11 is comparable to that in Comparative Referential Example 2 but there is a big difference in reaction time.

[Effect of the Invention]

The present invention permits the efficient production of α-olefins containing linear α-olefins in extremely high purity. The α-olefins will find use as comonomers for polyolefins (whose demand is increasing recently) and also as raw materials of synthetic lubricants.

The process of the present invention is superior to the conventional process, which involves replacement of trialkyl aluminum with butene in the presence of α-olefin, in that the resulting α-olefins have a high purity. This effect is due to the fact that (1) the butene displacement reaction does not give rise to branched olefins and (2) the ethylene growth that employs tributyl aluminum and ethylene hardly gives rise to branched olefins. (1) will be understood by comparing Example 2 with Comparative Example 2. (2) will be understood by comparing the conventional process with the process of the present invention.

The process of the present invention involves replacement of triethyl aluminum with butene for the production of tributyl aluminum. This displacement reaction gives rise to a mixture composed of ethylene, butene (unreacted product), tributyl aluminum, and triethyl aluminum. Needless to say, it is possible to reduce the amount of unreacted product to zero. It follows, therefore, that the process of the present invention, in principle, does not give rise to branched olefins which lower the purity of the desired α-olefins. In addition, the process of the present invention permits tributyl aluminum to be separated easily in pure form. Thus, the growth of ethylene by tributyl aluminum can be accomplished in the bare presence of olefins (other than ethylene). If growth is carried out in the presence of olefins other than ethylene, they also take part in growth to give an organoaluminum compound containing branched alkyl groups. This lowers the purity of the desired α-olefins.

The conventional process, which employs trialkyl aluminum formed in the ethylene growth for displacement with butene, gives rise to a reaction product of replacement which are composed of olefins, tributyl aluminum, and trialkyl aluminum (which remains unreacted).

Tributyl aluminum can be separated only in the form of mixture containing olefins of carbon number 16 and 18, because it is thermally unstable and has a boiling point close to that of olefins of carbon number 16 and 18.

An example of the conventional process is shown in FIG. 1 of Japanese Patent Laid-open No. 48630/1991. It involves the separation of tributyl aluminum in the form of mixture containing olefins of carbon number 12 and above, and this mixture is recycled to the ethylene growth step. In other words, according to the conventional process, it was inevitable that the growth of ethylene by tributyl aluminum is carried out in the presence of olefins other than ethylene. Growth of ethylene in the presence of olefins other than ethylene tends to form branched olefins, as mentioned above.

What is claimed is:

1. A process of producing an α-olefin which comprises carrying out separately the growth of ethylene with triethyl aluminum and the growth of ethylene with tributyl aluminum, displacing the resulting higher trialkyl aluminum with ethylene, thereby forming triethyl aluminum and an α-olefin, and displacing at least part of the resulting triethyl aluminum with butene contained in the resulting α-olefin, thereby forming tributyl aluminum.

2. A process of producing an α-olefin as defined in claim 1, wherein the triethyl aluminum and tributyl aluminum respectively obtained from the ethylene displacement reaction and/or butene displacement reaction are recycled to the ethylene growth step.

3. A process of producing an α-olefin as defined in claim 1, wherein the growth of ethylene with triethyl aluminum is the first ethylene growth step in which triethyl aluminum and ethylene are reacted with each other in the first ethylene growth reactor to give higher trialkyl aluminum and α-olefins.

4. A process of producing an α-olefin as defined in claim 1, wherein the growth of ethylene with tributyl aluminum is the second ethylene growth step in which tributyl aluminum and ethylene are reacted with each other in the second ethylene growth reactor to give higher trialkyl aluminum and α-olefins.

5. A process of producing an α-olefin as defined in claim 1, wherein the growth of ethylene with triethyl aluminum is the first ethylene growth step in which triethyl aluminum and ethylene are reacted with each other in the first ethylene growth reactor to give higher trialkyl aluminum and α-olefins, the growth of ethylene with tributyl aluminum is the second ethylene growth step in which tributyl aluminum and ethylene are reacted with each other in the second ethylene growth reactor to give higher trialkyl aluminum and α-olefins, and the products obtained by the first and second ethylene growth steps are distilled separately or all together for separation into light fractions containing no higher trialkyl aluminum and heavy fractions containing higher trialkyl aluminum in the first separation step.

6. A process of producing an α-olefin as defined in claim 5, wherein the displacement with ethylene is the ethylene displacement step which is intended to react ethylene with the heavy fractions separated in the first separation step to give triethyl aluminum and α-olefins.

7. A process of producing an α-olefin as defined in claim 6, wherein the product obtained in the ethylene displacement step is distilled for separation into light fractions containing no triethyl aluminum, triethyl aluminum, and heavy fractions containing no triethyl aluminum in the second separation step, the light fractions obtained by the first and second ethylene growth steps are distilled separately or all together for separation into ethylene and α-olefins of carbon number 4 and above in the third separation step, and the butene obtained in the third separation step and the all or part of triethyl aluminum obtained in the second separation step are reacted with each other in the butene displacement reactor to give tributyl aluminum and ethylene in the butene displacement step.

8. A process of producing an α-olefin as defined in claim 7, which further comprises the fourth separation step to distill the product obtained in the butene displacement step for separation into tributyl aluminum, unreacted triethyl aluminum, unreacted butene, and ethylene.

9. A process of producing an α-olefin as defined in claim 8, wherein the triethyl aluminum obtained in the second separation step is all or partly recycled to the first ethylene growth step and the tributyl aluminum obtained in the fourth separation step is recycled to the second ethylene growth step.

10. A process of producing an α-olefin as defined in claim 8, wherein the tributyl aluminum obtained in the fourth separation step is recycled to the second ethylene growth step and the unreacted triethyl aluminum obtained in the fourth separation step is recycled to the first ethylene growth step.

11. A process of producing an α-olefin as defined in claim 1, which comprises:

(1) the first ethylene growth step for reacting triethyl aluminum with ethylene in the first ethylene growth reactor to give higher trialkyl aluminum and an α-olefin, (2) the second ethylene growth step for reacting tributyl aluminum with ethylene in the second ethylene growth reactor to give higher trialkyl aluminum and an α-olefin.

(3) the first separation step for distilling separately or all together the products obtained in the first and second ethylene growth steps for separation into light fractions containing no higher trialkyl aluminum and heavy fractions containing higher trialkyl aluminum, (4) the ethylene displacement step for reacting ethylene with the heavy fraction obtained in the first separation step in the ethylene displacement reactor to give triethyl aluminum and an α-olefin, (5) the second separation step for distilling the product obtained in the ethylene displacement reaction for separation into light fractions containing no triethyl aluminum, triethyl aluminum, and heavy fractions containing no triethyl aluminum, (6) the third separation step for distilling separately or all together the light fraction obtained in the first separation step and the light fraction obtained in the second separation step for separation into ethylene and α-olefins of carbon number 4 and above, (7) the butene displacement step for reacting the butene obtained in the third separation step and the all or part of triethyl aluminum obtained in the second separation step in the butene displacement reactor to give tri-butyl aluminum and ethylene, and (8) the fourth separation step for distilling the product obtained in the butene displacement step for separation into tributyl aluminum, unreacted triethyl aluminum, unreacted butene, and ethylene.

12. A process of producing an α-olefin as defined in claim 11, which further comprises the hexene displacement step for reacting the hexene obtained in the third separation step and part of the triethyl aluminum obtained in the second separation step in the hexene displacement reactor to give trihexyl aluminum and ethylene, the fifth separation step for distilling the product obtained in the hexene displacement step for separation into trihexyl aluminum and ethylene, and the third ethylene growth step for reacting the trihexyl aluminum and ethylene in the second ethylene displacement reactor to give higher trialkyl aluminum and an α-olefin.

13. A process of producing an α-olefin as defined in claim 9, wherein the tributyl aluminum obtained in the fourth separation step is recycled to the second ethylene growth step and the unreacted triethyl aluminum obtained in the fourth separation step is recycled to the first ethylene growth step.

* * * * *